US008426487B2

(12) United States Patent
Shin et al.

(10) Patent No.: US 8,426,487 B2
(45) Date of Patent: Apr. 23, 2013

(54) FLUORINE-BASED COMPOUNDS AND COATING COMPOSITIONS COMPRISING THE SAME

(75) Inventors: Chong-Kyu Shin, Daejeon (KR); Yeong-Rae Chang, Daejeon (KR); Joon-Koo Kang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 238 days.

(21) Appl. No.: 13/119,919

(22) PCT Filed: Sep. 18, 2009

(86) PCT No.: PCT/KR2009/005338
§ 371 (c)(1),
(2), (4) Date: Mar. 18, 2011

(87) PCT Pub. No.: WO2010/032990
PCT Pub. Date: Mar. 25, 2010

(65) Prior Publication Data
US 2011/0165404 A1 Jul. 7, 2011

(30) Foreign Application Priority Data

Sep. 19, 2008 (KR) ........................ 10-2008-0092332

(51) Int. Cl.
*B32B 27/32* (2006.01)
*C07F 7/04* (2006.01)
*C04B 24/26* (2006.01)

(52) U.S. Cl.
USPC ........... 522/160; 522/153; 428/220; 556/441; 524/523

(58) Field of Classification Search ................ 522/153, 522/160; 428/220; 556/441; 524/523; 560/81
See application file for complete search history.

(56) References Cited

U.S. PATENT DOCUMENTS
2002/0106582 A1* 8/2002 Xu et al. ..................... 430/270.1
2002/0115820 A1* 8/2002 Wang et al. .................. 528/401

FOREIGN PATENT DOCUMENTS
JP 2006-002136 5/2006
WO WO 00/35998 * 6/2000

\* cited by examiner

*Primary Examiner* — Michael Pepitone
*Assistant Examiner* — Jessica Paul
(74) *Attorney, Agent, or Firm* — McKenna Long & Aldridge, LLP

(57) ABSTRACT

The present invention provides a fluorine-based compound and a coating composition and a film including the same. By using the fluorine-based compound according to the present invention, a film having excellent functionalities of water repellency, oil repellency, weatherability and contamination resistance can be provided.

14 Claims, 2 Drawing Sheets

FLUORINE-BASED COMPOUNDS AND COATING COMPOSITIONS COMPRISING THE SAME

TECHNICAL FIELD

This application claims the priority to PCT/KR2009/005338 filed on Sep. 18, 2009 and Korean Patent Application No. 10-2008-0092332 filed on Sep. 19, 2008, all of which are hereby incorporated by reference in their entirety. The present invention relates to a fluorine-based compound. More particularly, the present invention pertains to a fluorine-based compound that has excellent functionalities of water repellency, oil repellency, weatherability and contamination resistance, and a coating composition including the same.

BACKGROUND ART

A fluorine-based compound has very low surface energy of about 5 to 6 dyne/cm to provide functionalities of water repellency, oil repellency, chemical resistance, lubricating properties, releasing properties and contamination resistance. The fluorine-based compound having the functionalities may be extensively used in the range from special fields, such as high-technology industries and fine chemicals, to daily lives, and, recently, a demand for the compound has been rapidly growing. Particularly, in accordance with the spread of personal computers and the general use of vehicles, an effort has been actively conducted to develop materials protecting surfaces of materials from external contaminants. Silicon compounds or fluorine compounds are extensively used as raw materials of surface coating agents used to protect surfaces of the compounds.

However, the coating agent formed only using a known silicon compound has a poor reaction crosslinking property of inorganic oxides and, thus, friction durability is poor or desirable crosslinking depending on the number of functional groups forming 3-D structures is not obtained. Therefore, the glass transition temperature Tg thereof is low, contaminants are easily collected thereon, and fingerprints may remain by hands.

In addition, the coating agent formed only using the fluorine compound has a poor contaminant removal ability. In order to avoid the poor contaminant removal ability, the silane compound having a perfluorine group is used as a surface reforming agent. However, the compound is not capable of having all of desirable water repellency, oil repellency, antifouling ability, and contaminant removal abilities.

DISCLOSURE

Technical Problem

It is an object of the present invention to provide a fluorine-based compound that has excellent functionalities of water repellency, oil repellency, weatherability and contamination resistance, and a coating composition including the same.

Technical Solution

The present invention provides a fluorine-based compound that is represented by Formula 1:

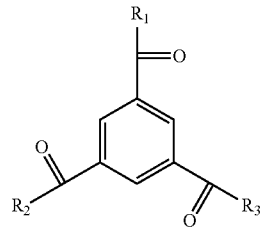

[Formula 1]

wherein $R_1$ is $CF_3(CF_2)_x(CH_2CH_2)_y(OCH_2CH_2)_z$—O— ($0 \leq x<100$, $0 \leq y<100$, and $0 \leq z<100$) or

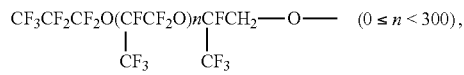

$(0 \leq n < 300)$, $R_2$ is the same as $R_1$, or a group derived from a (meth)acryl-containing compound or a group derived from a silicon-containing compound, and
$R_3$ is a group derived from a (meth)acryl-containing compound or a silicon-containing compound.

The present invention provides a coating composition that includes a binder resin; and the fluorine-based compound.

The present invention provides a film that includes a binder resin; and the fluorine-based compound.

Advantageous Effects

A fluorine-based compound according to the present invention has excellent functionalities of water repellency, oil repellency, weatherability and contamination resistance. Therefore, a film having excellent water repellency, oil repellency, weatherability and contamination resistance is provided using the same.

BEST MODE

Figure 1:
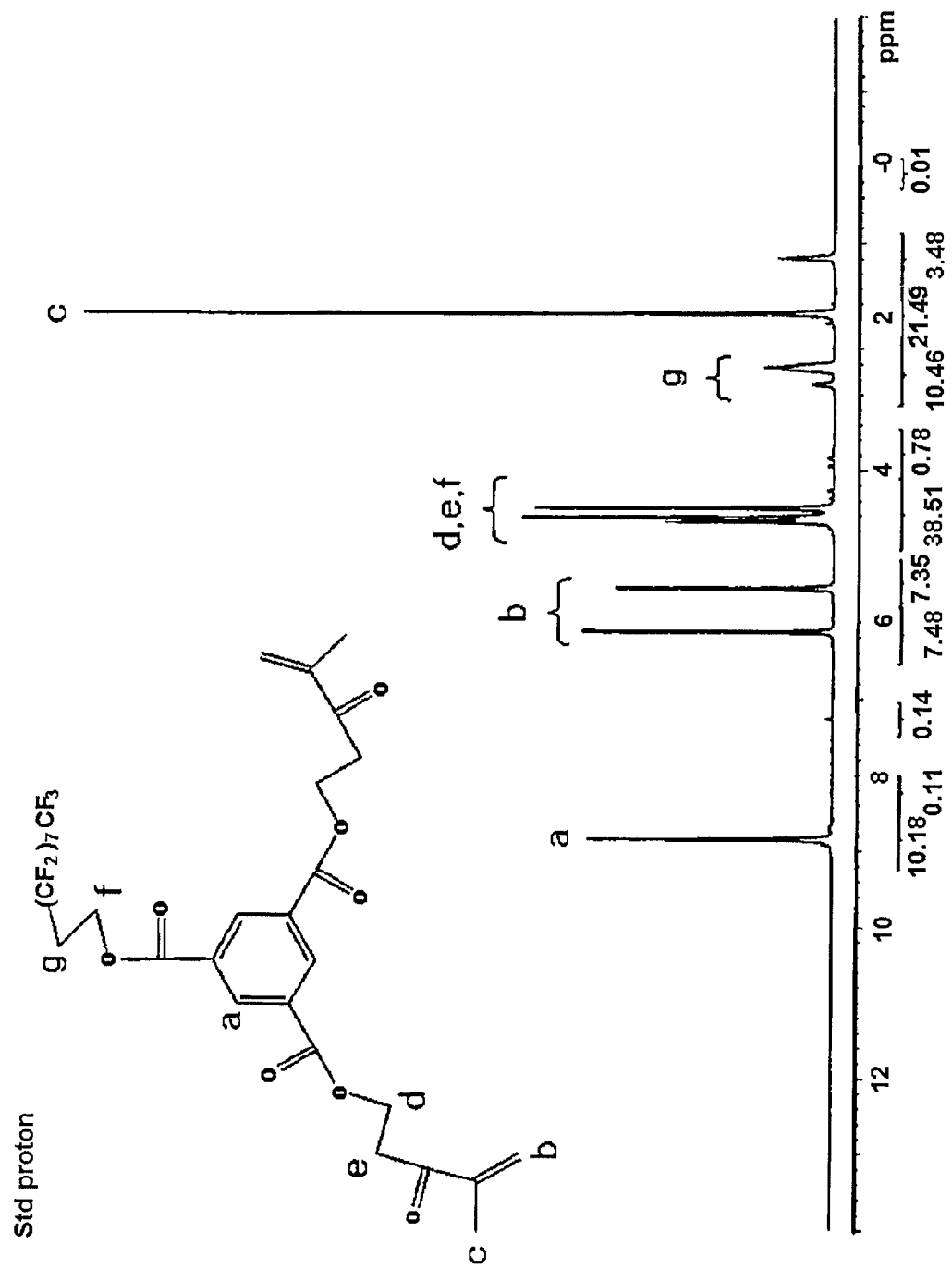
FIG. 1 is NMR data of a fluorine-based compound according to Example 1.

A fluorine-based compound according to the present invention is a compound that is represented by Formula 1:

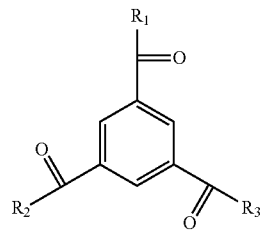

[Formula 1]

wherein $R_1$ is $CF_3(CF_2)_x(CH_2CH_2)_y(OCH_2CH_2)_z$—O— ($0 \leq x < 100$, $0 \leq y < 100$, and $0 \leq z < 100$) or

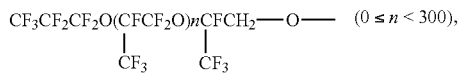
$CF_3CF_2CF_2O(CFCF_2O)_nCFCH_2$—O—  ($0 \leq n < 300$),
with $CF_3$ substituents $R_2$ is the same as $R_1$, or a group derived from a (meth)acryl-containing compound or a group derived from a silicon-containing compound, and
$R_3$ is a group derived from a (meth)acryl-containing compound or a silicon-containing compound.

The (meth)acryl-containing compound may be UV-curable. Particularly, the (meth)acryl-containing compound may be one or more selected from the group consisting of (meth)acrylic acid, methyl(meth)acrylate, ethyl(meth)acrylate, butyl(meth)acrylate, hexyl(meth)acrylate, dodecyl(meth)acrylate, stearyl(meth)acrylate, benzyl(meth)acrylate, and cyclohexyl(meth)acrylate.

The silicon-containing compound may be heat-curable. Particularly, the silicon-containing compound may be one or more selected from the group consisting of $CH_2$=$C(CH_3)CO_2(CH_2)_3Si(OCH_3)_3$, $CH_2$=$CHSi(OC_2H_5)_3$, $CH_2$=$C(CH_3)CO_2(CH_2)_3Si(CH_3)(OCH_3)_2$, $CH_2$=$CHCO_2(CH_2)_3Si(OCH_3)_3$, $CH_2$=$CHSi(OCH_3)$, $CH_2$=$C(CH_3)CO_2(CH_2)_3Si(CH_3)(OC_2H_5)_2$, $CH_2$=$C(CH_3)CO_2(CH_2)_3Si(OC_2H_5)_3$, and $CH_2$=$CHCH_2Si(CH_3)_3$.

In the present invention, a group that is "derived from" a compound means a group in a state in which at least one of the substituent groups including hydrogen of the compound is removed and thus can be covalent bonded to the core structure of Formula 1.

In the present invention, the term "(meth)acryl" includes methacryl and acryl.

The fluorine-based compound according to the present invention may provide water repellency, oil repellency, weatherability, and antifouling ability, and may improve water repellency, oil repellency, weatherability, and antifouling ability.

The coating composition according to the present invention includes a binder resin; and the fluorine-based compound.

The content of the fluorine-based compound may be 0.1 to 99.9 parts by weight based on 100 parts by weight of the binder resin.

The binder resin may be a UV curable functional group-containing binder resin. The UV curable functional group-containing binder resin may include multifunctional or monofunctional monomers or oligomers of acrylates, methacrylates or vinyls.

The UV curable functional group-containing binder resin is a main component that is capable of providing wear resistance to the coating film. It is preferable that the binder resin have high crosslinking density to improve wear resistance. However, when the crosslinking density is very high, a crack according to curing shrinkage of the coating film or poor adhesion may occur. Accordingly, the crosslinking density needs to be appropriately controlled.

Examples of acrylates include dipentaerythritol hexaacrylate, pentaerythritol tetraacrylate, pentaerythritol triacrylate, trimethylene propyltriacrylate, ethylene glycol diacrylate, hexanediol diacrylate, ethyl acrylate, ethylhexyl acrylate, butyl acrylate, and hydroxyethyl acrylate.

Examples of acrylate oligomers include urethane denatured acrylate oligomers, epoxy acrylate oligomers, and ether acrylate oligomers, and it is preferable that the number of functional groups of acrylate is 2 to 6. It is preferable that the molecular weight of the oligomer is 100 to 10,000.

Examples of the methacrylates include trimethylolpropane trimethacrylate, ethylene glycol dimethacrylate, butanediol dimethacrylate, hexaethyl methacrylate, and butyl methacrylate, and methacrylate oligomers may be used.

Examples of vinyls include divinyl benzene, styrene, and para-methyl styrene.

The binder resin is a heat curable functional group-containing binder resin, and may include a siloxane resin.

The fluorine-based compound represented by Formula 1 is a main component added to the coating composition to provide water repellency, oil repellency, weatherability, and antifouling ability.

The coating composition according to the present invention may further include a polymerization initiator. In connection with this, the content of the fluorine-based compound may be 0.1 to 99.9 parts by weight and a content of the polymerization initiator may be 1 to 20 parts by weight based on 100 parts by weight of the binder resin.

The content of the polymerization initiator may be 1 to 20 parts by weight, and preferably 2 to 8 parts by weight. The content of the polymerization initiator of 20 or less parts by weight advantageously prevents the properties of the film from deteriorating. The content of the polymerization of 1 or more parts by weight advantageously cause sufficient crosslinking.

The polymerization initiator may be a photo-initiator or a heat-initiator.

The photo-initiator is not limited as long as the photo-initiator is capable of being decomposed by UV. Specific examples thereof may include Igacure 127, Igacure 184, Igacure 1173, and Igacure 2959 of alpha-hydroxy ketones, Igacure 369, Igacure 379, Igacure 907, and Igacure 1300 of alpha-aminoketones, Igacure 651 of benzyldimethyl ketal, and Darocure TPO of monoacyl phosphine. It is preferable that the content of the photo-initiator is 1 to 20 parts by weight based on 100 parts by weight of the binder resin.

The heat initiator is not limited as long as the heat initiator is capable of being decomposed by heat. Specific examples thereof may include a dilute hydrochloric acid.

The coating composition according to the present invention may further include a solvent.

The coating composition according to the present invention may further include a solvent to ensure a coating property in addition to the aforementioned components. The type or content of the solvent is not limited.

Examples of the solvent include alcohol, alkane, ether, cycloalkane, and other aromatic organic solvents. Specific examples thereof include, but are not limited to methanol, ethanol, isopropyl alcohol, butanol, ethylene glycol, diacetone alcohol, 2-ethoxyethanol, 2-methoxyethanol, 2-butoxyethanol, propyleneglycol monomethyl ether, hexane, heptane, cyclohexane, acetyl acetone, dimethyl ketone, methylethyl ketone, methyl isobutyl ketone, toluene, benzene, xylene, methyl acetate, ethyl acetate, butal acetate, dimethyl formamide, and tetrahydropurane.

It is preferable that the content of the solvent is 1 to 99 parts by weight based on 100 parts by weight of the binder resin.

The coating composition according to the present invention may be applied on the substrate. Examples of the substrate are not limited, but include a plastic film. Examples of the film include polyester, triacetyl cellulose, olefin copolymers, polymethyl methacrylate.

The coating composition may be applied on the substrate using a known coating process. Non-limiting examples of the coating process include 2 roll reverse coating, 3 roll reverse coating, gravure coating, microgravure coating, die coating, curtain coating, bar coating, dip coating, and flow coating.

It is preferable that the film coated by the process is cured in the UV intensity of 0.05 to 2 J/cm$^2$ after drying. Particularly, when the curing is performed at a nitrogen atmosphere, the degree of surface curing may be increased to improve antifouling property.

The coating thickness of the coating composition is preferably 0.01 to 300 micrometers, 0.1 to 30 micrometers, and more preferably 0.5 to 10 micrometers. The abrasion resistance is improved as the coating thickness is increased, but curling or cracks may occur due to the curing shrinkage.

The film according to the present invention may be a film including a binder resin; and the fluorine-based compound according to the present invention. In addition, the coating composition may further include the polymerization initiator, and the coating film may be a film including a binder resin; the fluorine-based compound; and the coating composition including the polymerization initiator. The above description is applied to the above embodiment.

The thickness of the film may be 0.01 to 300 micrometers, preferably 0.1 to 30 micrometers, and preferably 0.5 to 10 micrometers.

The substrate may be provided on a side of the film.

The film including the fluorine-based compound represented by Formula 1 according to the present invention has all of desirable water repellency, oil repellency, weatherability, and antifouling abilities.

The film according to the present invention has preferably a contact angle of 120 or more degrees.

The film according to the present invention may be applied without a limit as long as the film is used to provide water repellency, oil repellency, weatherability, and antifouling ability, and, for example, the film may be applied to display devices. The coating film may be directly applied on parts of target devices such as display devices, or may be applied to the target devices in conjunction with the substrate after the film is formed on the substrate. The coating film according to the present invention may be applied to liquid crystal displays, organic light emitting displays (OLED), and plasma display panels (PDP), but the scope of the present invention is not limited thereto. Examples of display apparatuses including the display devices include, but are not limited to monitors for computer, notebook computers, and mobile phones.

MODE FOR INVENTION

A better understanding of the present invention may be obtained in light of the following Examples which are set forth to illustrate, but are not to be construed to limit the present invention.

Example 1

Preparation of the Acryl-Containing Fluorine-Based Compound 1

5.37 g of 1,3,5-benzenetricarboxyl trichloride and 30 mL of HCFC225 were added to the 100 mL flask including the thermometer and agitating apparatus, and agitated at room temperature and a nitrogen atmosphere. After 1,3,5-benzenetricarboxyl trichloride was dissolved in HCFC225, 11.40 g of perfluoro alcohol (average molecular weight 564 g/mol) was added to the reaction solution. Subsequently, 2.25 g of triethylamine was slowly dropped. After the reaction solution was agitated for 1 hour, 5.31 g of 2-hydroxyethyl methacrylate was dropped. After 10 min, 5.50 g of triethylamine was slowly dropped. Subsequently, after the agitation for 1 hour, the precipitate was filtered to remove, and HCFC225 was removed by distillation to obtain 21.4 g of the colorless/transparent acryl-containing fluorine-based compound 1. NMR data of the obtained compound are shown in FIG. 1.

Example 2

Preparation of the Silicon-Containing Fluorine-Based Compound 2

Figure 2:
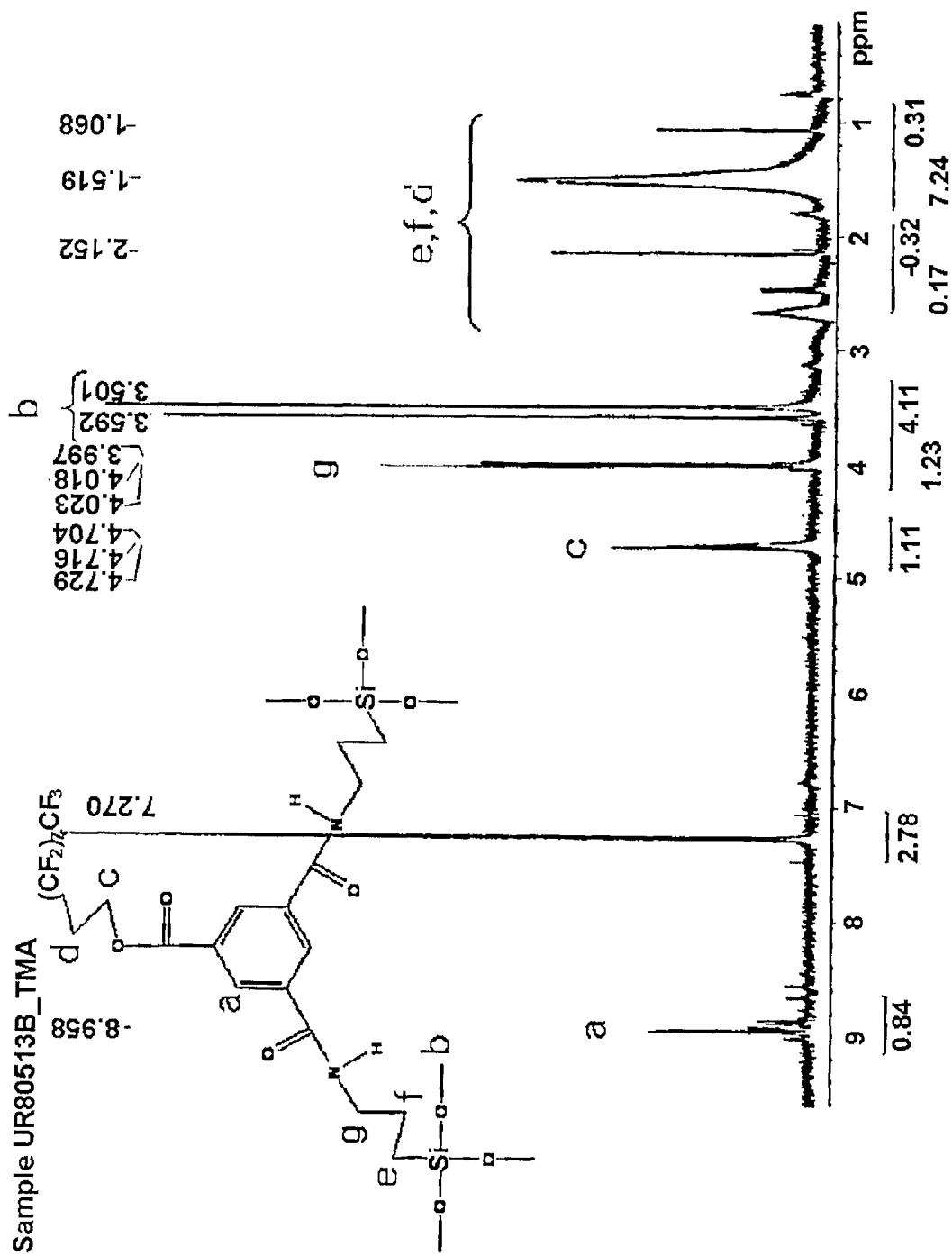
FIG. 2 is NMR data of a fluorine-based compound according to Example 2.

5.37 g of 1,3,5-benzenetricarboxyl trichloride and 30 mL of HCFC225 were added to the 100 mL flask including the thermometer and agitating apparatus, and agitated at room temperature and a nitrogen atmosphere. After 1,3,5-benzenetricarboxyl trichloride was dissolved in HCFC225, 11.40 g of perfluoro alcohol (average molecular weight 564 g/mol) was added to the reaction solution. Subsequently, 2.25 g of triethylamine was slowly dropped. After the reaction solution was agitated for 1 hour, 7.30 g of 3-aminopropyltrimethoxysilane was dropped and agitated for 1 hour. The precipitate of the solution was filtered to remove, and HCFC225 was removed by distillation to obtain 23.4 g of the colorless/transparent silicon-containing fluorine-based compound 2. NMR data of the obtained compound are shown in FIG. 2.

Experimental Example 1

Preparation of the Sample 1

After the acryl-containing fluorine-based compound prepared in Example 1 was dissolved using the methyl ether ketone solvent so that the concentration thereof is 1 wt %, a small amount of photo-initiator was added thereto to prepare the acryl-containing fluorine-based compound solution for UV curing. After the acryl-containing fluorine-based compound solution for UC curing was applied on the polyether (PET) film, the solvent was vaporized in the oven at 50 C for 10 min, and UV was radiated thereonto to perform the curing.

Experimental Example 2

Preparation of the Sample 2

Meanwhile, the silicon-containing fluorine-based compound prepared in Example 2 was dissolved using the methyl ether ketone solvent so that the concentration thereof is 1 wt % to prepare the silicon-containing fluorine-based compound solution for heat curing. After the acryl-containing fluorine-based compound solution for heat curing was applied on the polyether (PET) film, the solvent was vaporized in the oven at 50° C. for 10 min, and the they were completely cured at 120° C. for 5 min.

Measurement of Physical Properties

The contact angle for the samples prepared in Experimental Examples 1 and 2 was measured in distilled water at 20° C. using Goniometer having the light radiation apparatus. The measurement was performed in respects to five different drops having the contact drop diameter of 2 mm, and the average values thereof were recorded. The measured contact angles of the compound samples are described in Table 1.

TABLE 1

| Classification | contact angle (deg.) |
| --- | --- |
| Sample 1 (compound 1) | 121.2 |
| Sample 2 (compound 2) | 120.8 |

The invention claimed is:

1. A fluorine-based compound that is represented by Formula I:

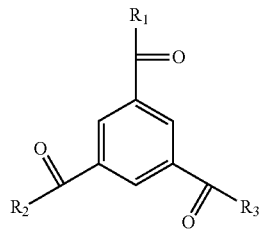

[Formula 1]

wherein $R_1$ is $CF_3(CF_2)_x(CH_2CH_2)_y(OCH_2CH_2)_z$—O— and wherein $0 \leq x < 100$, $0 \leq y < 100$, and $0 \leq z < 100$ or

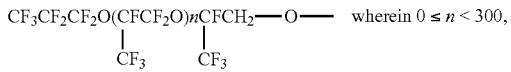

wherein $0 \leq n < 300$, $R_2$ is the same as $R_1$, or a group derived from a (meth)acryl-containing compound or a group derived from a silicon-containing compound, and $R_3$ is a group derived from a (meth)acryl-containing compound or a silicon-containing compound.

2. The fluorine-based compound as set forth in claim 1, wherein the (meth)acryl-containing compound is one or more selected from the group consisting of (meth)acrylic acid, methyl (meth)acrylate, ethyl (meth)acrylate, butyl (meth)acrylate, hexyl (meth)acrylate, dodecyl (meth)acrylate, stearyl (meth)acrylate, benzyl (meth)acrylate, and cyclohexyl (meth)acrylate.

3. The fluorine-based compound as set forth in claim 1, wherein the silicon-containing compound is one or more selected from the group consisting of $CH_2\!=\!C(CH_3)CO_2(CH_2)_3Si(OCH_3)_3$, $CH_2\!=\!CHSi(OC_2H_5)_3$, $CH_2\!=\!C(CH_3)CO_2(CH_2)_3Si(CH_3)(OCH_3)_2$, $CH_2\!=\!CHCO_2(CH_2)_3Si(OCH_3)_3$, $CH_2\!=\!CHSi(OCH_3)$, $CH_2\!=\!C(CH_3)CO_2(CH_2)_3Si(CH_3)(OC_2H_5)_2$, $CH_2\!=\!C(CH_3)CO_2(CH_2)_3Si(OC_2H_5)_3$, and $CH_2\!=\!CHCH_2Si(CH_3)_3$.

4. A coating composition comprising:
a binder resin; and
the fluorine-based compound according to claim 1.

5. The coating composition as set forth in claim 4, wherein a content of the fluorine-based compound is 0.1 to 99.9 parts by weight based on 100 parts by weight of the binder resin.

6. The coating composition as set forth in claim 4, further comprising:
a polymerization initiator.

7. The coating composition as set forth in claim 6, wherein the polymerization initiator is a photo-initiator or a heat-initiator.

8. The coating composition as set forth in claim 6, wherein a content of the fluorine-based compound is 0.1 to 99.9 parts by weight and a content of the polymerization initiator is 1 to 20 parts by weight based on 100 parts by weight of the binder resin.

9. The coating composition as set forth in claim 4, wherein the binder resin is a UV curable functional group-containing binder resin and includes multifunctional or monofunctional monomers or oligomers of acrylates, methacrylates or vinyls.

10. The coating composition as set forth in claim 4, wherein the binder resin is a heat-curable functional group-containing binder resin and includes a siloxane-based resin.

11. The coating composition as set forth in claim 4, further comprising:
a solvent.

12. A film comprising:
a binder resin; and
the fluorine-based compound according to claim 1.

13. The film as set forth in claim 12, wherein a thickness of the film is 0.01 to 300 micrometers.

14. The film as set forth in claim 12, wherein the film has a contact angle of 120 or more degrees.

* * * * *